(12) United States Patent
Kiguchi et al.

(10) Patent No.: US 8,103,332 B2
(45) Date of Patent: Jan. 24, 2012

(54) HEAD-COUPLED HOLDER FOR LIVING BODY OPTICAL MEASUREMENT

(75) Inventors: Masashi Kiguchi, Kawagoe (JP); Naoki Matsushima, Yokohama (JP); Hirokazu Atsumori, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 711 days.

(21) Appl. No.: 12/219,259

(22) Filed: Jul. 18, 2008

(65) Prior Publication Data

US 2009/0054789 A1 Feb. 26, 2009

(30) Foreign Application Priority Data

Aug. 21, 2007 (JP) ................. 2007-214919

(51) Int. Cl.
*A61B 6/00* (2006.01)
(52) U.S. Cl. ...................................... 600/476
(58) Field of Classification Search ............ None
See application file for complete search history.

(56) References Cited

U.S. PATENT DOCUMENTS

| 2001/0018554 A1 | 8/2001 | Yamashita et al. |
| 2002/0028997 A1 | 3/2002 | Ito et al. |
| 2002/0095089 A1 | 7/2002 | Yamamoto et al. |
| 2004/0054271 A1 | 3/2004 | Maki et al. |
| 2004/0077935 A1* | 4/2004 | Hirabayashi et al. ......... 600/310 |
| 2004/0236226 A1* | 11/2004 | Maki et al. .................... 600/473 |

FOREIGN PATENT DOCUMENTS

| EP | 1447049 A1 | 5/2002 |
| EP | 1407711 A1 | 8/2003 |
| JP | 9-149894 | 12/1995 |
| JP | 2000-172407 | 12/1998 |
| JP | 2002-172106 | 12/2000 |

* cited by examiner

*Primary Examiner* — Brian Casler
*Assistant Examiner* — Saurel J Selkin
(74) *Attorney, Agent, or Firm* — Stites & Harbison PLLC; Juan Carlos A. Marquez, Esq.

(57) ABSTRACT

A head-coupled holder the optical measurement of a living body that securely brings a light irradiation module and a light detection module in close contact with the scalp of a person to be examined, and gives the person no excessive pressure feeling. Each light irradiation module and light detection module includes a contactor having a contact portion that comes in contact with the scalp at a leading end thereof, and exposes a leading end of a light guide to the contact portion to form the light guide, and a package having a lower portion to which the contactor is attached. The contactor is fixed to the lower portion of the package through an elastic body, and the package is fixed to an inner upper wall of the insertion hole with a series structure of the elastic body and the viscoelastic body.

8 Claims, 8 Drawing Sheets

HEAD-COUPLED HOLDER FOR LIVING BODY OPTICAL MEASUREMENT

CLAIM OF PRIORITY

The present application claims priority from Japanese patent application JP 2007-214919 filed on Aug. 21, 2007, the content of which is hereby incorporated by reference into this application.

FIELD OF THE INVENTION

The present invention relates to a living body optical measurement system that measures an internal state of a living body by the use of light, and more particularly to a head-coupled holder for optical measurement of brain functions by analysis of the intensity of light that passes through a head of a living person to be examined.

BACKGROUND OF THE INVENTION

As means for measuring the brain functions of a human body, there has been developed an optical topographic technique that analyzes the intensity of a return near-infrared light which has been applied to a part of the head and then passes through the head to two-dimensionally display the blood distribution of the cerebral cortex. The above technique proves the correspondence of the motor functions of a human body and the localized regions of the brains, to thereby find a clue as to a new psychiatric treatment. Also, in recent years, there has been advanced the development of an interface technique that directly controls an external device such as a computer, a game machine, or an environmental control unit by the aid of a measurement signal from the brain with the use of localized brain functions. For example, JP-A-1997-149894 has proposed a method of measuring the intensity of head transmitted light by the aid of a living body optical measuring device, calculating the quantity of oxygenated and reduced hemoglobin by means of an arithmetic device, and driving the external device by the aid of calculated data. JP-A-2000-172407 has proposed a method of determining the history of changes in measurement signals that have been obtained from the living body optical measuring device by the aid of the arithmetic device, a storage device, or a control unit, and applying the discrimination results to a specific rule to change over the channels of a television receiver. Also, JP-A-2002-172106 has proposed an interface technique of bringing an optical irradiator and a photodetector in contact with the skin of a body to be examined, and controlling an object of a screen according to the intensity of the obtained light signals.

SUMMARY OF THE INVENTION

In the case of precisely conducting the living object measurement by using the techniques mentioned previously, it is remarkably important that the quantity of irradiated light is held constant, and light other than the light returned from the head is prevented from being input to the photodetector. When those conditions cannot be satisfied, a ratio (S/N ratio) of the signal light to the noise light cannot be held to a high value, thereby making it impossible to conduct a precise evaluation. In order to solve the above problem, the light irradiation portion of a light irradiation module and the light introduction portion of a photodetector module must be securely brought in close contact with the head, and those portions must also be fixed so as not to move. However, the configuration of the head is substantially spherical, the leading end of the module must reach the scalp around the hairs, and the module must be adjusted to diverse shapes because the configuration of the head is different depending on the person to be examined. For that reason, the module needs to be held against the head with a significant force in order to securely prevent the module from moving. However, there is a case in which when the module is fixed to the head with a strong force, the person to be examined may feel a strong pressure, and cannot withstand the measurement for a long time. There is the possibility that this causes an obstacle to the measurement in everyday life or a condition close to everyday life. Also, the person to be examined of old age, an infant, or a young child may not withstand the wearing of the module due to the pressure feeling, and therefore the measurement per se cannot be conducted.

An object of the present invention is to provide a head-coupled holder for the optical measurement of a living body which securely brings a light irradiation/light detection module in close contact with a scalp, and does not give the feeling of excessive pressure to the person to be examined in order to enable precise optical measurement of the person to be realized for all of persons to be examined and in all of measurement configurations.

Each light irradiation module and light detection module which are equipped in the head-coupled holder for optical measurement includes a contactor having a contact portion that comes in contact with the scalp of a person to be examined at a leading end thereof, and exposes a leading end portion to the contact portion to form a light guide, and a package having a lower portion to which the contactor is attached. Also, the holder has an insertion hole having a lower portion opened into which the package is inserted. In one embodiment of the present invention, the contactor is fixed to the lower portion of the package through an elastic body, and the package is fixed to an inner upper wall of the insertion hole through the elastic body. In another embodiment, the package is fixed to the inner upper wall of the insertion hole through a tandem structure consisting of the elastic body and a viscoelastic body. In this case, it is preferable that the contactor is fixed to the lower portion of the package through the elastic body. In still another embodiment, the contactor is fixed to the lower portion of the package through the elastic body, and the package is fixed to the inner upper wall of the insertion hole through the viscoelastic body.

It is preferable that the elastic body that connects the package and the holder is of a spring structure such as a spring coil or a plate spring. It is preferable that the tandem connection structure of the elastic body that connects the package and the holder, and the viscoelastic body, or the viscoelastic body is made of a resin that mainly contains any component of urethane resin, vinyl resin, and silicon resin. Similarly, it is suitable that the elastic body that connects the contactor and the package is formed of a spring.

According to the present invention, the light irradiation portion of the light irradiation module or the light introduction portion of the light detection module can be excellently brought in close contact with the scalp without applying an excessive force to the head of the person to be examined, thereby improving the measurement precision of the living body optical measurement. Also, because the uncomfortable feeling of the person to be examined who wears the holder can be also remarkably reduced, it is possible to wear the holder for a long time, wear the holder in a state close to the everyday life, and the holder worn by an older person, an infant, or a young child as the person to be examined, thereby remarkably enlarging the measurable range of optical measurement of living bodies that can be accomplished.

DETAILED DESCRIPTION OF THE PREFERRED EMBODIMENTS

Figure 1:
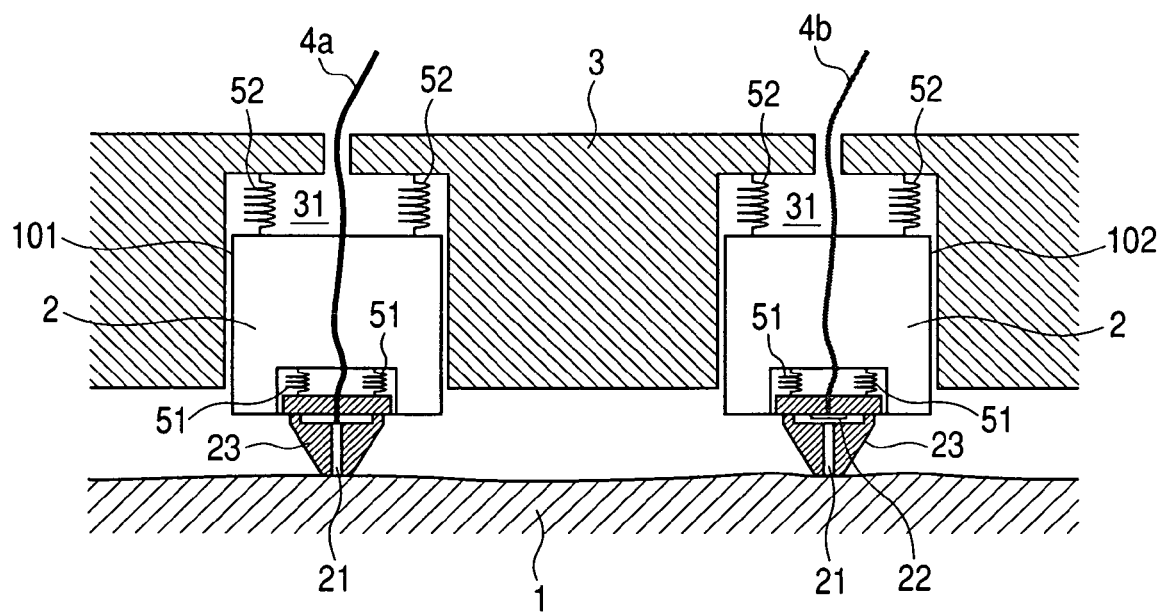
FIG. 1 is a schematic diagram showing a first embodiment of the present invention.

Hereinafter, a description will be given of embodiments of the present invention with reference to the accompanying drawings. The substantially same parts are denoted by identical reference numerals, and their description will not be repeated.

First Embodiment

Figure 2:
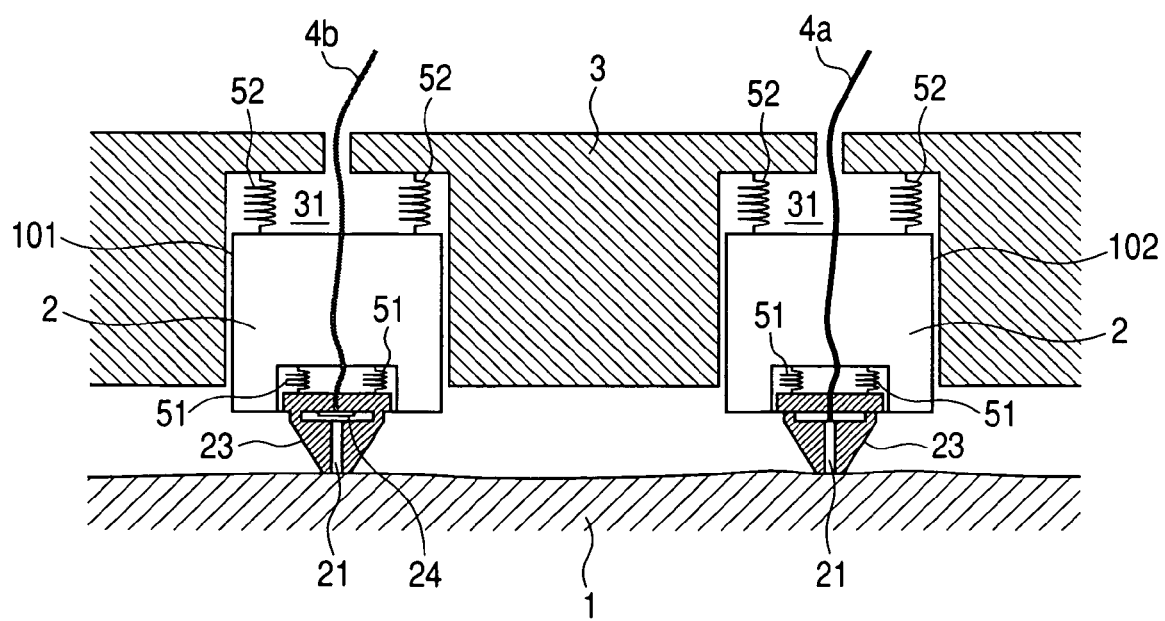
FIG. 2 is a diagram showing a modified example of FIG. 1.

A first embodiment of the present invention will be described with reference to FIGS. 1 and 2. FIG. 1 schematically shows a head-coupled holder for optical measurement of a living body having a light irradiation module 101 and a light detection module 102 in a living body optical measuring device. The numbers of light irradiation modules and light detection modules are one in FIG. 1, respectively, but plural modules can be provided, respectively. In this example, the light detection module 102 shown on a right side of the drawing will be described. In the drawing, reference numeral 1 denotes a head (scalp) of a person to be examined, 2 is a package of a module, 3 is a holder that fixes the package 2, and 4b is a cable for connecting the module and a control unit module. The package 2 is made of rigid resin such as vespel (R) (polyimide), and inserted into a package insertion hole 31 that is defined in a lower surface of the holder 3. The lower portion of the package 2 is fitted with a contactor having a light guide 21 for introducing the light that has been applied from the light irradiation module 101 and propagated through the head into a photodetector. The light that has been guided into the light guide 21 is applied to the photodetector 22 such as a photodiode which is located at an end of the light guide opposite to the scalp side, and then converted into an electric signal. The electric signal is propagated in a cable 4b through an electric circuit which is disposed within the light detection module so as to be transmitted to the control unit. The light guide 21 and the photodetector 22 are fixed so as not to change their positional relationship.

The contactor 23 having the light guide 21 which is in contact with the scalp is connected to the package 2 of the module through elastic bodies 51. Also, the module package 2 and the holder 3 are connected to each other through elastic bodies 52. The package 2 stores a photonic device and an electronic circuit for photoelectric conversion therein, and serves as a guide for guiding an optical fiber to the control unit.

The drawings of the elastic bodies shown in the figure and viscoelastic bodies that will be described later are schematic drawings for schematically illustrating those bodies, and do not always coincide with real configurations. Also, the numbers of elastic bodies and viscoelastic bodies in the figure are two, respectively, however, the numbers of those bodies can be one, or three or more. The same is applied to second and subsequent embodiments.

The contactor 23 that is in contact with the scalp is connected with the cable 4b (an optical fiber 4a in the case of the light irradiation module 101). In this case, there is applied a structure in which a bend section that ensures a stroke that is equal to or larger than a displacement of the elastic body, or the optical fiber is not fixed to the package 2, so as not to apply an unreasonable force to the cable or the optical fiber. The same is applied to the second and subsequent embodiments.

The fixation to the head is conducted in such a manner that the holder 3 is thrust into the scalp 1 while wrapping around the head, and the leading end of the contactor 23, that is, the leading portion of the light guide 21 is brought into contact with the scalp 1 due to the restoring forces of the elastic bodies 51 and 52. It is preferable that the holder is made of resin or fabric that is liable to be deformed so as to follow the configuration of the head of the person to be examined. Alternatively, the holder can be made of a net-shaped material. However, a material that readily changes a distance between those modules should not be used. Because the contactor 23 is thinly shaped, the leading end of the contactor 23 can be brought in contact with the scalp without being disturbed by hairs though the hairs exist on the scalp. In this situation, the respective entire packages are thrust into the scalp by the elastic bodies 52 that connect the holder 3 and the package 2. Because the head of the person to be examined is not of a complete spherical shape, there is the possibility that the thrust pressures of the respective optical modules are varied in the case of using only the elastic bodies 51. When the thrust pressure is small, the leading end of the contactor 23 cannot be brought in sufficient close contact with the scalp when the thrust pressure is small, resulting in a risk that the measurement is varied. In the present invention, because the elastic bodies 51 that connect the light guide 21 and the package 2 is disposed in each of the modules in addition to the elastic bodies 52, the leading end of the light guide 21 in each of the optical modules follows the head, respectively, thereby making it possible to bring each of the optical modules in close contact with the scalp without applying an excessive pressure to the scalp. Accordingly, it is possible to conduct the optical measurement of a living body without applying an unnecessary load on the person to be examined.

In an example of FIG. 1, the photodetector 22 is disposed within the light detection module 102. Also, as far as the light irradiation module 101 is concerned, no light emitting device is disposed within the module, the optical fiber 4a is connected between the module and the control unit, and a light emitting device is located in the control unit or between the control unit and the light irradiation module although being not shown. Alternatively, as shown in FIG. 2, the light detection module 102 extracts the signal through the optical fiber 4a, and the photodetector is located in the control unit or between the control unit and the light detection module. The light irradiation module 101 has a light emitting device 24 within the module, and the light emitting device 24 and the control unit are connected to each other by the cable 4b. It is needless to say that each of the modules can have the photonic device, or none of the modules can have the photonic device.

Figure 13A:
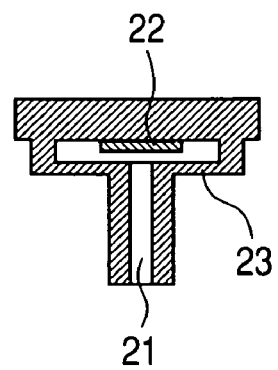
FIG. 13A and FIG. 13B are diagrams showing examples of the configuration of the contactor, respectively.
Figure 13B:
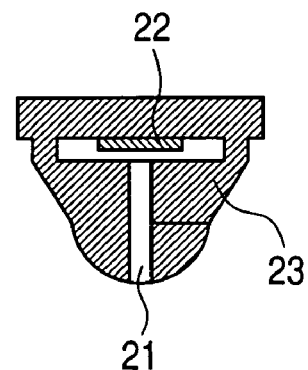

The contactor 23 is made of a relatively hard material so as not to be remarkably deformed. The material of the contactor 23 is not particularly limited, but a lightweight material such as resin is preferable taking that a load which is applied to the person to be examined is reduced as much as possible into consideration. Also, in this embodiment, the contactor 23 is of a conic configuration whose diameter is gradually more thinned toward the scalp. However, other configurations can be applied when the contactor 23 can be brought in close contact with the scalp while preventing from being disturbed by hairs. Some examples of the configuration are shown in FIGS. 13A and 13B. FIG. 13A shows a contactor having a leading end that is cylindrically configured, and FIG. 13B shows a contactor having a conic configuration which is gradually smaller in diameter toward the scalp as a whole, and having a scalp contact portion curved. It is preferable that the dimensions of the portion of the contactor 23 which is brought in contact with the scalp are set to about 0.5 to 5 mm. The light guide 21 that is disposed in the interior of the contactor 23 needs to be made of a material which well transmits the irradiated or detected near-infrared light. More specifically, the light guide 21 can be formed of a transparent resin bar, a glass bar, an optical fiber, or a bundle fiber that bundles the optical fibers.

With the use of the holder having the light irradiation module and the light detection module according to this embodiment, the light irradiation module or the light detection module can be excellently brought in close contact with the scalp without applying an excessive force to the head of the person to be examined, to thereby improve the measurement precision of the living body optical measurement system. Also, because the uncomfortable feeling of the person to be examined is remarkably reduced, it is possible to wear the holder in an everyday life state, and have an infant, a young child, or an older person as the person to be examined, thereby remarkably enlarging the measurable range of optical measurement that can be done on living bodies.

Second Embodiment

Figure 3:
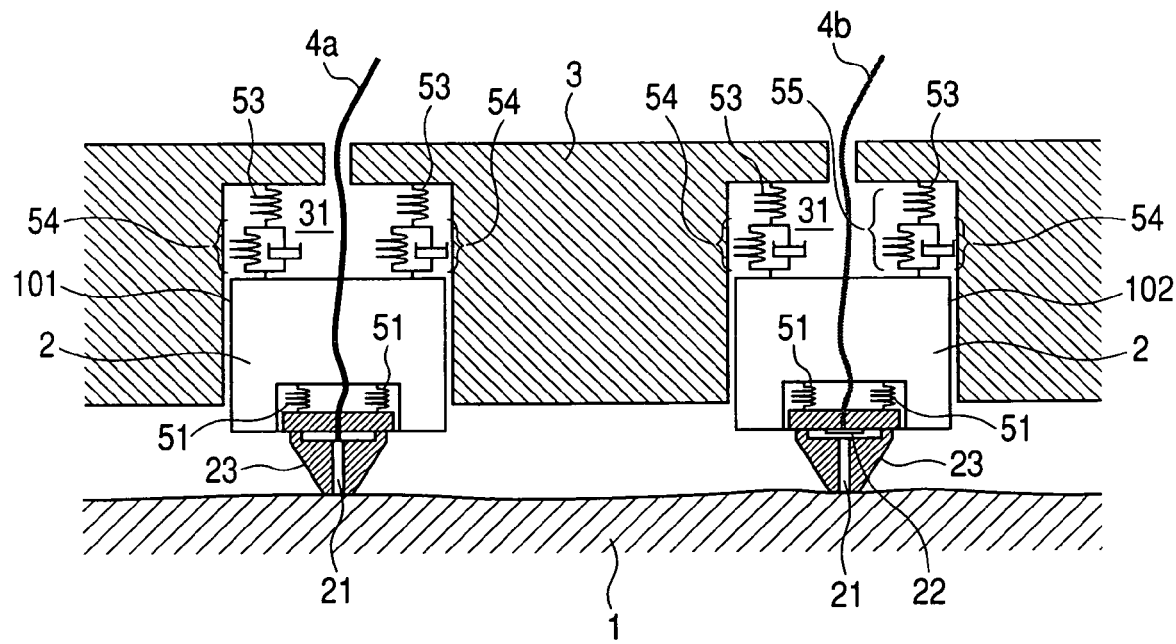
FIG. 3 is a schematic diagram showing a second embodiment of the present invention.

Now, a description will be given of a second embodiment of the present invention with reference to FIGS. 3 to 5. FIG. 3 schematically shows a part of a head-coupled holder for a living body optical measuring device with the same configuration as that of FIG. 1. A difference from FIG. 1 resides in that a portion that connects the package 2 and the holder 3 is formed of a member 55 that connects an elastic body 53 and a viscoelastic body 54 in series.

The viscoelastic body is made of a material having both properties of viscosity and elasticity. More specifically, a creep phenomenon in which the viscoelastic body is gradually deformed with application of a certain stress, and a stress relaxation phenomenon in which the stress is gradually reduced when the viscoelastic body is displaced to some degree are actions specific to the viscoelastic body. On the other hand, the elastic body is made of a material having a property that produces a restoring force proportional to the displacement when the elastic body is deformed by application of a stress, and returns the configuration to an original configuration immediately after the stress has been removed.

Figure 4:
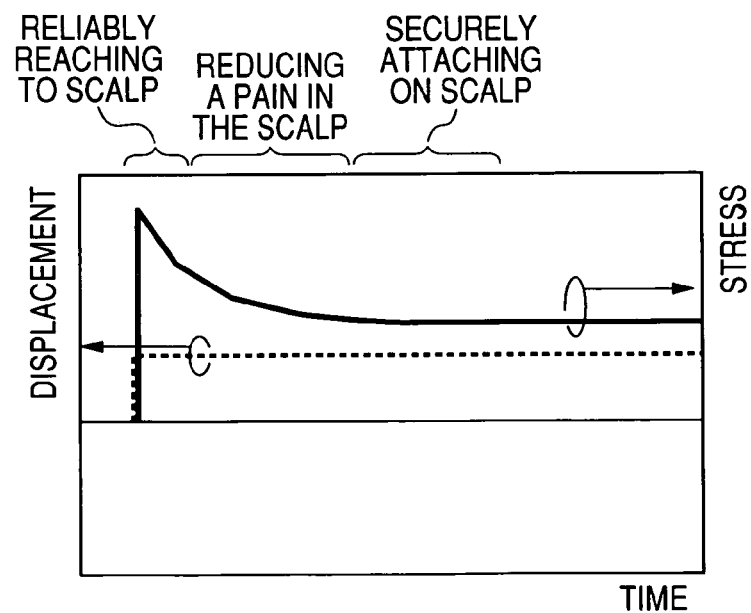
FIG. 4 is a graph showing a change in a pressure applied to a scalp of a person to be examined with time.

FIG. 4 is a graph showing a change in a pressure (stress) that is applied to the scalp of the person to be examined with time when the holder according to this embodiment is worn on the head of the person to be examined. When it is assumed that the thrust quantity of the holder 3, that is, the amounts of displacement of the elastic body 53, the viscoelastic body 54, and the elastic body 51 that connects the contactor 23 and the package 2 are held constant, the restoring force of the entire elastic body components is exerted immediately after the holder has been worn on the head, and the stress that is applied to the head represents a relatively high value. The leading end of the light guide 21 in each of the modules is securely brought in contact with the scalp due to the above pressure. Thereafter, the pressure is gradually attenuated. This is because the dashpot component of the viscoelastic body is gradually displaced to relax the stress. Finally, the pressure is held constant to a certain pressure. A reduction in the pressure reduces a load on the person to be examined. Also, since the pressure becomes finally a constant pressure value, the worn holder is prevented from being detached from the head.

When the holder is really fixed to the head, the holder 3 is first thrust on the scalp 1 while wrapping around the head. In this situation, the pressure that is applied to the scalp is temporarily larger as shown in FIG. 4. This force enables the module leading end to be readily brought in contact with the scalp 1 combined with the configuration of the contactor 23 even if the irregularity or the hairs exist on the head. Also, the module leading end can follow the head configuration by the aid of the elastic body 51 which connects the contactor 23 and the package 2 with respect to the local irregularity of the head. Thereafter, the pressure that is applied to the scalp is reduced by the displacement of the viscoelastic body when the holder 3 is fixed, as shown in FIG. 4. As a result, the uncomfortable feeling of the person to be examined can be reduced even if the contact area of the contactor 23 leading end having the light guide 21 with the scalp is smaller. Then, the pressure is converged to a given value. Since the constant pressure is applied to the scalp, and the leading end follows the local irregularity of the head due to the elastic body 51, the contact of the scalp with the light guide 21 is ensured. That is, the use of the holder according to this embodiment enables the optical module to be excellently brought in close contact with the scalp without application of an excessive force to the head of the person to be examined, to thereby improve the measurement precision of the living body optical measurement. Also, because the uncomfortable feeling of the person to be examined is remarkably reduced, it is possible to wear the holder in an everyday life state, and have an infant, a young child, or an older person as the person to be examiner, thereby remarkably enlarging the measurable range of optical measurement that can be done on a living body.

Because the above mechanism is disposed in each of the modules, the wearing state is hardly varied, and any module can be surely brought in contact with the scalp.

Figure 5:
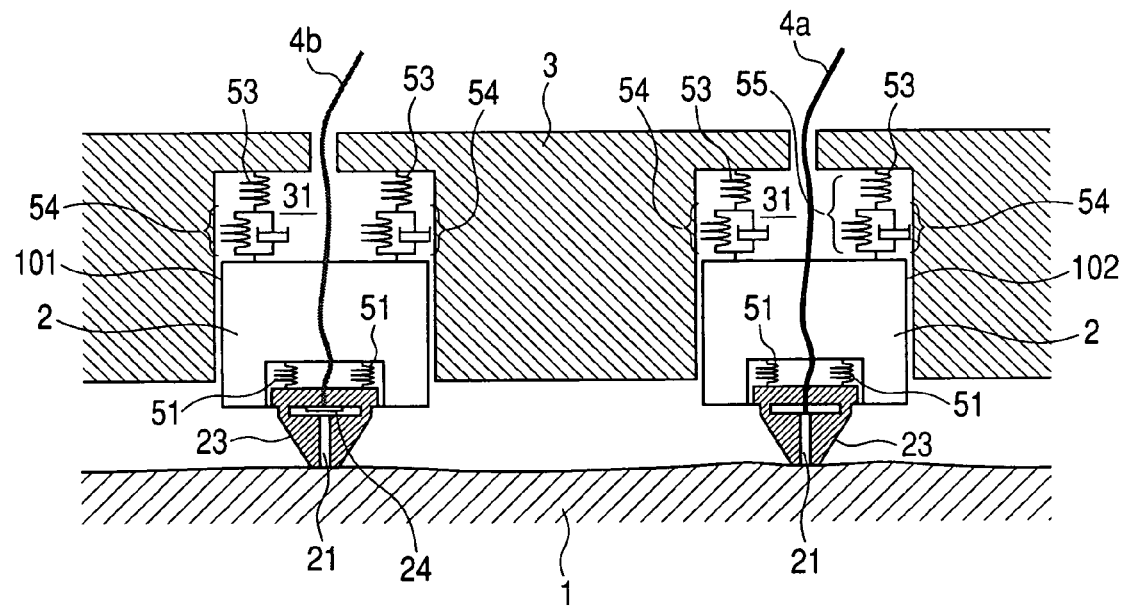
FIG. 5 is a diagram showing a modified example of FIG. 3.

The structure shown in FIG. 3 can be changed to a structure in which a light emitting device is disposed in the light irradiation module 101, and the light detection module 102 locates the photodetector in the control unit or between the control unit and the light detection module, as shown in FIG. 5. It is needless to say that both of the modules can provide the photonic device, or none of the modules can provide the photonic device. Also, the materials and configurations of the contactor 23 and the light guide 21 in this embodiment are identical with those in the first embodiment.

Third Embodiment

Figure 6:
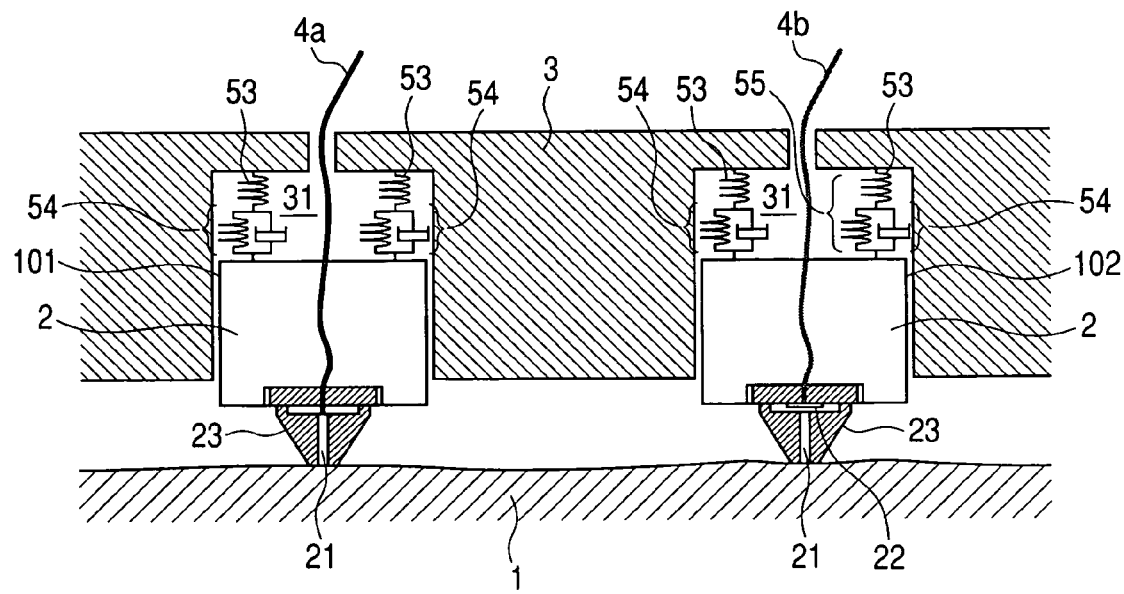
FIG. 6 is a schematic diagram showing a third embodiment of the present invention.

Now, a description will be given of a third embodiment of the present invention with reference to FIGS. 6 and 7. FIG. 6 shows a structure in which a portion that connects the package 2 and the holder 3 is formed of a member 55 that connects the elastic body 53 and the viscoelastic body 54 in series. The contactor 23 and the package 2 are rigidly fixed to each other.

Similarly, the structure shown in FIG. 6 is capable of realizing a change in the pressure with time as shown in FIG. 4. That is, the pressure becomes relatively high immediately after the holder has been worn on the head, which surely brings the leading end of the contactor 23 in each of the modules in close contact with the scalp. Thereafter, the pressure is gradually attenuated to reduce a load on the person to be examined. Further, the pressure is held to a given pressure value, thereby preventing the worn holder 3 from being uncoupled. Accordingly, the use of the holder according to this embodiment enables the light irradiation/light detection module to be excellently brought in close contact with the scalp without applying an excessive force to the head of the person to be examined as in the second embodiment. As a result, the measurement precision of the optical measurement of living bodies is improved. Also, the uncomfortable feeling of the person to be examined is remarkably reduced, and it is possible to wear the holder in an everyday life state, and conduct the measurement of an infant, a young child, or an older person as the person to be examined.

Figure 7:
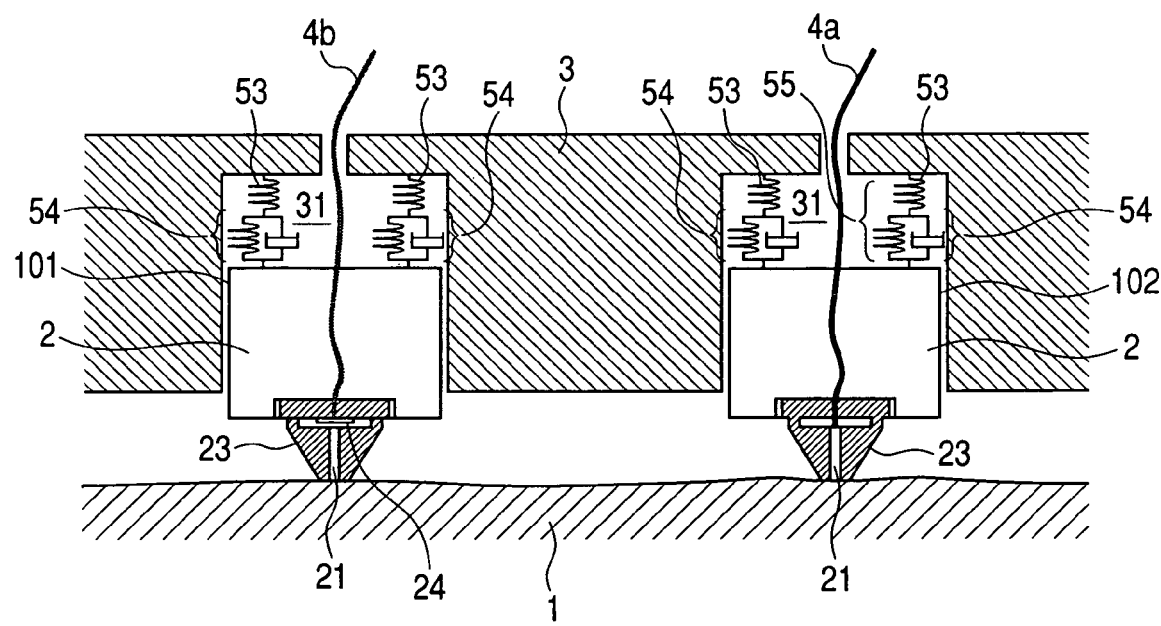
FIG. 7 is a diagram showing a modified example of FIG. 6.

The structure of FIG. 6 can be of a structure in which the light irradiation module 101 is equipped with the light emitting device 24, and the light detection module 102 locates the photodetector in the control unit or between the control unit and the light detection module, as shown in FIG. 7. It is needless to say that both of the modules can be equipped with the light emitting devices or no light emitting devices. Also, the materials and configurations of the contactor 23 and the light guide 21 are identical with those in the first embodiment.

Fourth Embodiment

Figure 8:
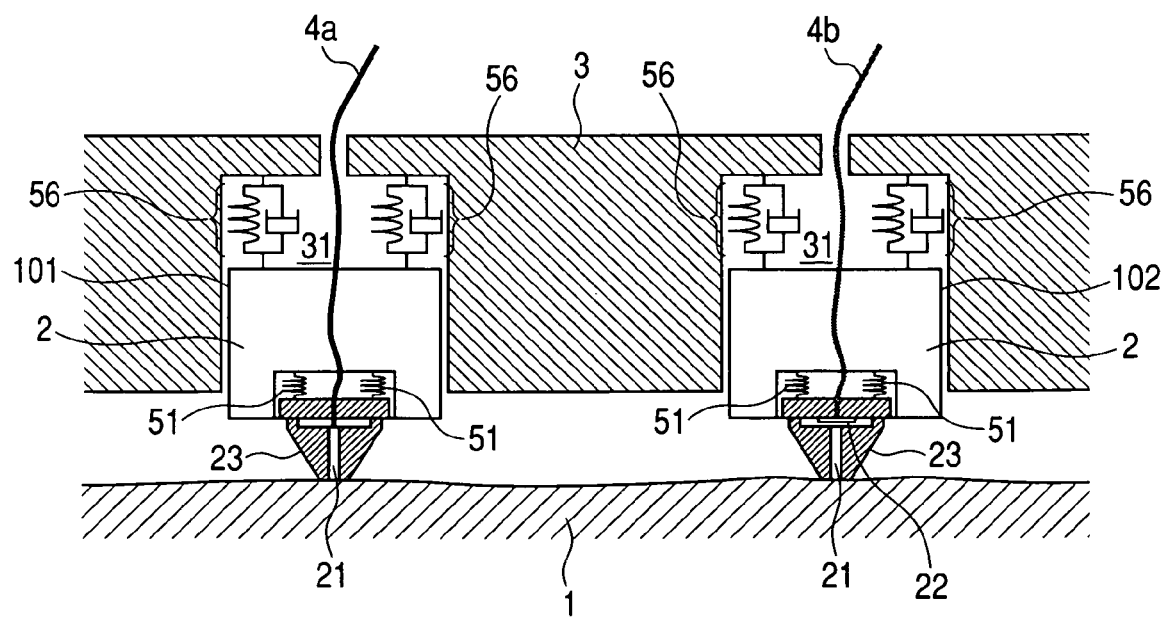
FIG. 8 is a schematic diagram showing a fourth embodiment of the present invention.

Now, a description will be given of a fourth embodiment of the present invention with reference to FIGS. 8 and 9. FIG. 8 shows a holder for a living body optical measuring device having the same configuration as that of FIG. 3. A different from FIG. 3 resides in that the portion that connects the package 2 and the holder 3 is formed of a viscoelastic body 56. A variation in the pressure which is applied to the scalp when this structure is worn on the head of the person to be examined is shown in FIG. 4 as in the second and third embodiments. That is, according to this embodiment, the measurement precision of the optical measurement system is improved without applying an excessive load on the head of the person to be examined as in the second and third embodiments. Also, because the uncomfortable feeling of the person to be examined is remarkably reduced, it is possible to wear the holder in an everyday life state, and have an infant or an older person as the person to be examined, thereby remarkably enlarging the measurable range of optical measurement that can be done on a living body.

Figure 9:
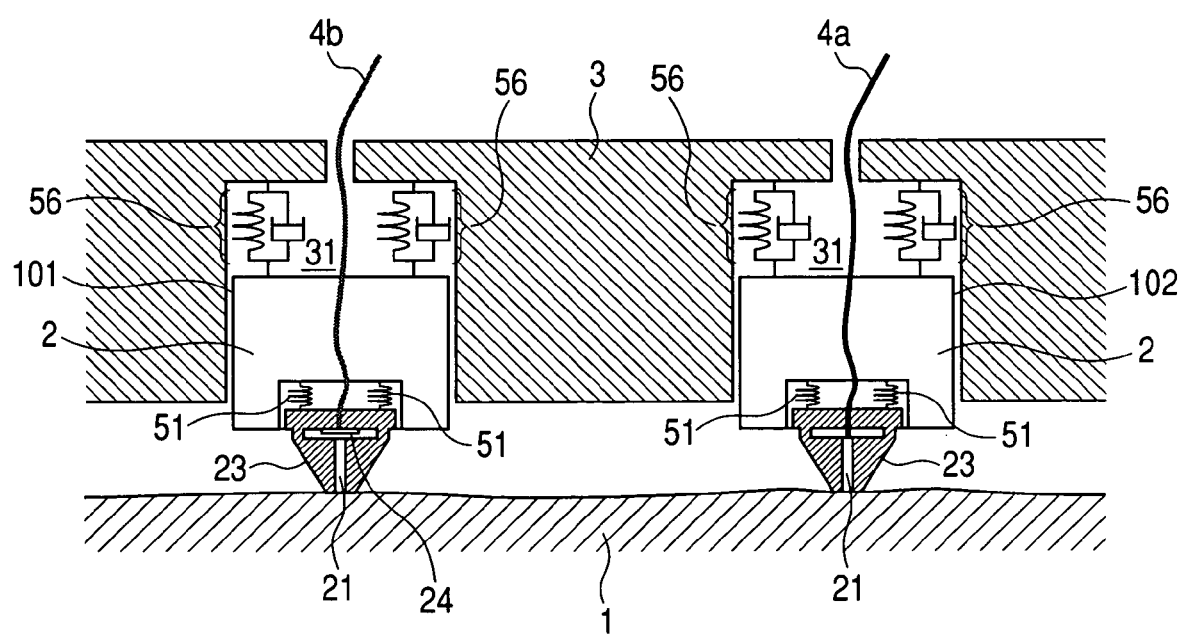
FIG. 9 is a diagram showing a modified example of FIG. 8.

This structure can be of a structure in which the light irradiation module 101 is equipped with the light emitting device 24, and the light detection module 102 locates the photodetector in the control unit or between the control unit and the light detection module, as shown in FIG. 9. It is needless to say that both of the modules can be equipped with the light emitting devices or no light emitting devices. The materials and configurations of the contactor 23 and the light guide 21 are identical with those in the first embodiment.

Fifth Embodiment

Now, a description will be given of a fifth embodiment of the present invention with reference to FIGS. 10A to 10C.

Figure 10A:
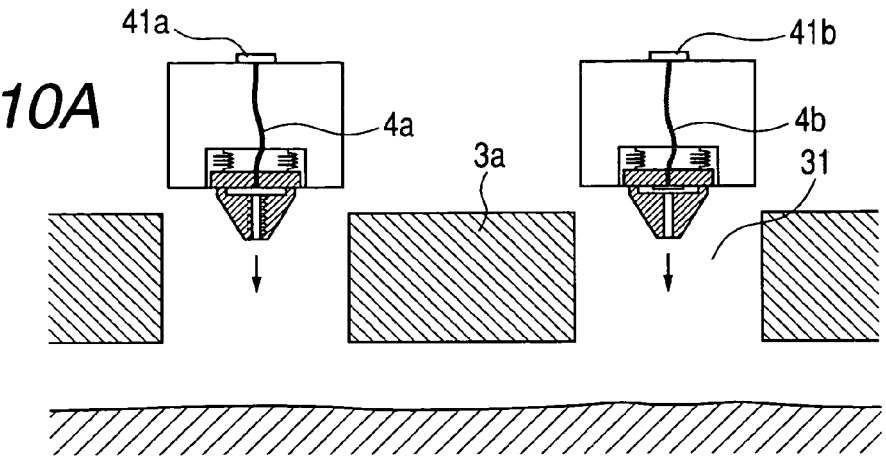
FIGS. 10A to 10C are schematic diagrams showing a configuration of the attachment and detachment of a light irradiation/light detection module.
Figure 10B:
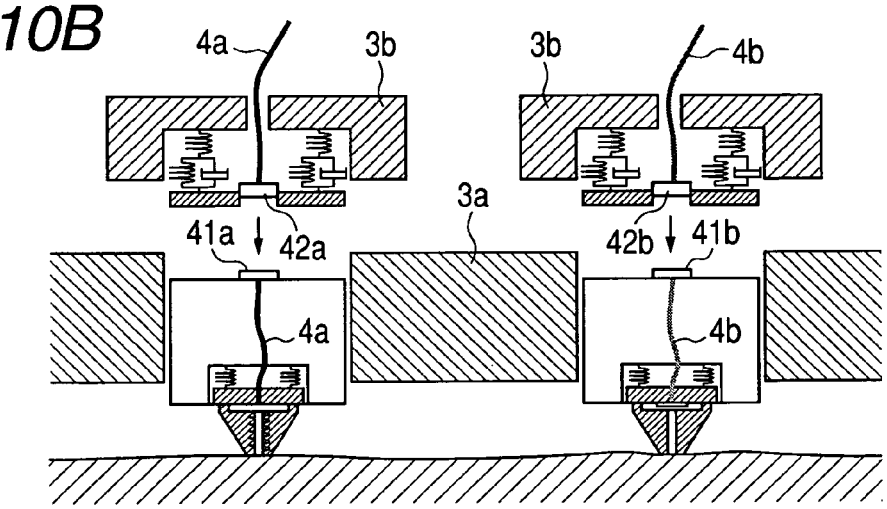
Figure 10C:
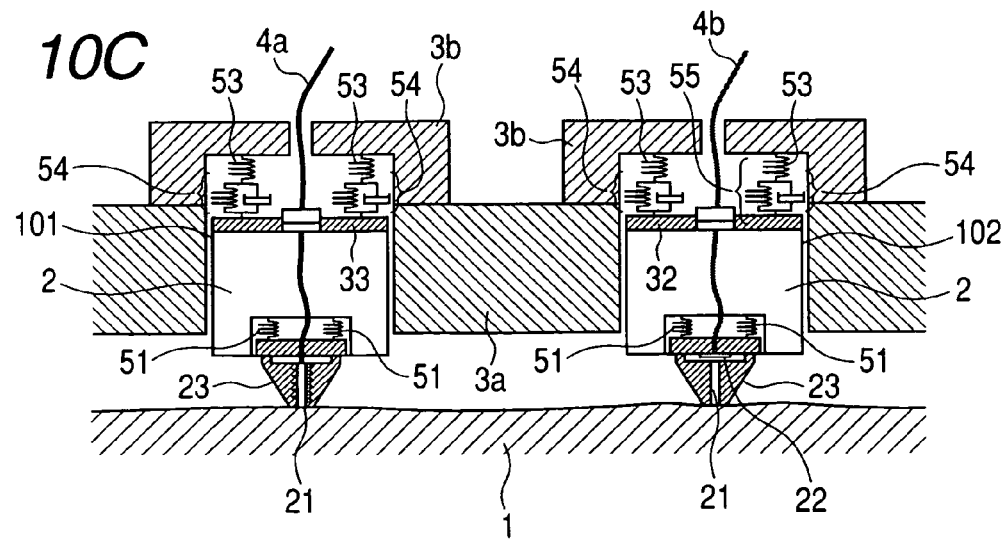

FIGS. 10A to 10C are schematic diagrams showing the configuration of attachment or detachment of the light irradiation module and the light detection module with respect to the holder in the living body optical measuring device according to the present invention. The configuration after the attachment is of the structure shown in FIG. 3.

FIG. 10A shows a state in which the light irradiation module and the light detection modules are not attached to the holder 3a. In the figure, the scalp 1 is drawn. The holder 3a can be worn on the head of the person to be examined before the modules are attached to the holder 3a as shown in the figure, or the holder 3a can be brought in close contact with the head after the modules have been attached to the holder 3a. The modules 101 and 102 are inserted into holes 31 that are defined in the holder 3a.

Then, as shown in FIG. 10B, a holder cap 3b for fixing the module to the holder is put on the top of each of the modules. The holder cap 3b is equipped with the member 55 having the elastic body and the viscoelastic body 54 connected in series to each other. One of portions of the holder cap 3b which are connected with the member 32 is fixed to the holder 3a at a fixing portion 32. Also, another portion is fixed to the package 2 at a fixing portion 33. The fixation of the holder 3a to the holder cap 3b can be conducted by screw fixation or snap. The fixation of the package to the holder cap can be conducted by using or adding connectors 41a/42a or 41b/42b of the optical fiber 4a or the electric wiring cable 4b.

Through the above procedure, the attachment of the holder 3 in the living body optical measuring device shown in FIG. 10C is completed. The living body optical measuring device that is mounted on the head in the above configuration enables the module leading end to be brought in close contact with the scalp without applying an excessive load to the person to be examined. As a result, the measurement precision is improved, and it is possible to wear the holder in an everyday life state, and have an infant or an older person as the person to be examiner, thereby remarkably enlarging the measurable range, as in other embodiments.

Sixth Embodiments

Figure 11:
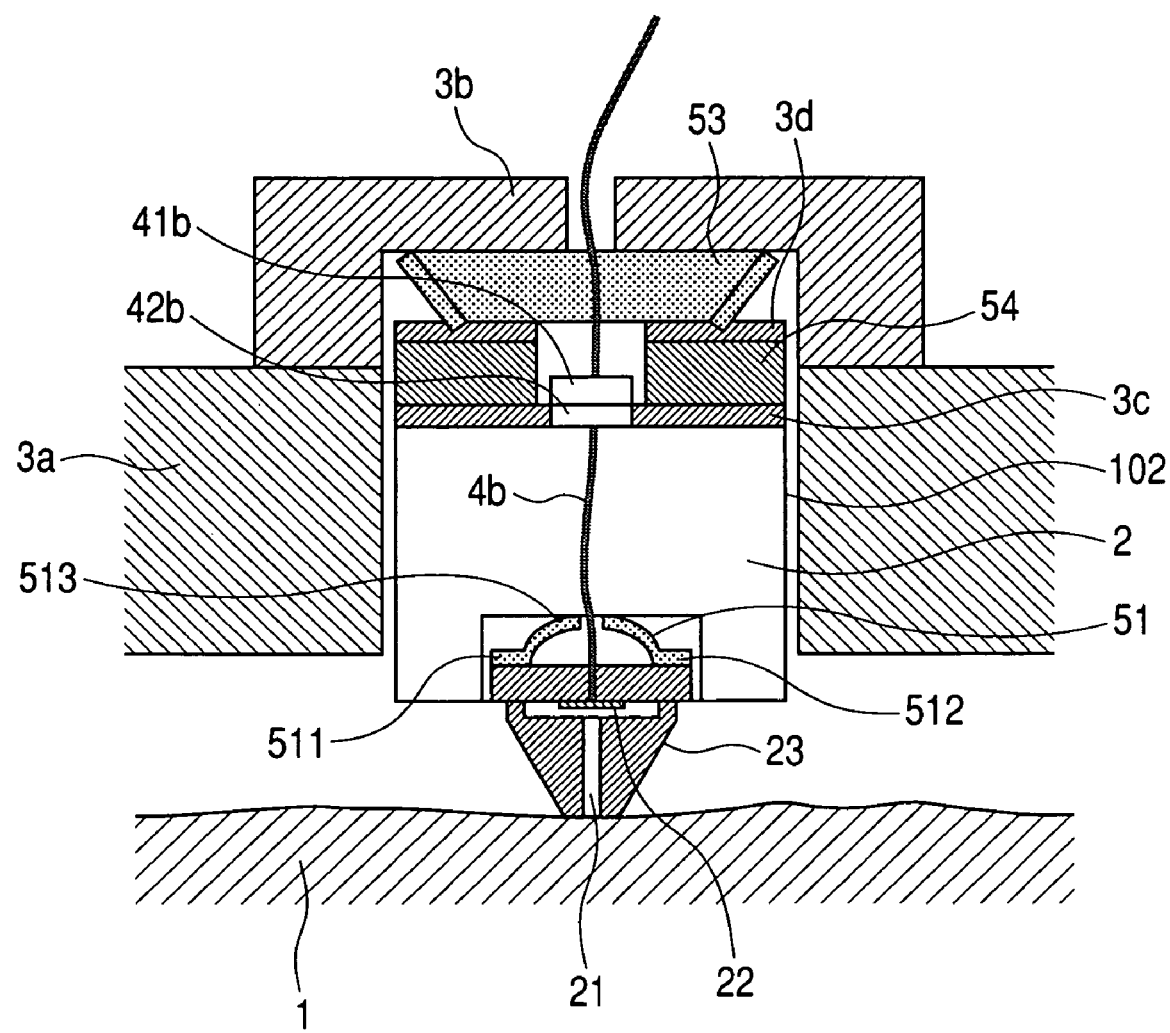
FIG. 11 is a schematic diagram showing a light detection module.

Now, a description will be given of a sixth embodiment of the present invention with reference to FIG. 11. FIG. 11 shows a schematic diagram of the light detection module 102 in the holder of the living body optical measuring device, and illustrates the elastic body and the portion of the elastic body according to the configuration of a real member, or in a state close to the real member. The parts that constitute the module are identical with those of FIG. 10 which is described in the fifth embodiment. In this drawing, only the light detection module is shown, but the same is applied to the light irradiation module.

In the figure, the package 2 is equipped with the contactor 23 having the light guide 21 for introducing the light that has been applied from the light irradiation module and propagated through the head into the photodetector. The light that has been introduced into the light guide 21 is applied to the photodetector 22 represented by a photodiode which is disposed at the leading end of the light guide opposite to the scalp side, and is then converted into an electric signal. The electric signal propagates in the cable 4b through an electric circuit within the light detection module, and is then transmitted to the control unit.

The light guide 21 and the photodetector 22 are fixed within the contactor 23 so as not to change their positional relationship. The contactor 23 and the package 2 of the module are connected to each other through the elastic body 51. In the figure, there is used a so-called "plate spring" in which steel is bent in an arc shape, and a force is applied to the arc steel in a direction of collapsing the arc to generate a restoring force as the elastic body 51. Both ends 511 and 512 of the spring plate are in contact with the contactor 23 for the scalp. The contact portions can be fixed by an adhesive, or can be thrust by the restoring force of the spring unless the contact portions are remarkably misaligned or a gap is produced in the contact portions. The plate spring 51 and the package 2 are brought in contact with each other by an arc portion 513 of the plate spring 51. A manner of fixing those members to each other is the same as that with respect to the member 23. The plate spring 51 is treated in order to avoid the cable 4*b* that extends from the detector 22 such that a hole is defined in a part of the plate spring 51 so as not to be obstructed by the cable 4*b*. In this embodiment, the plate spring is used, but the elastic body 51 can be formed of a spring having other configurations such as a coil spring or a disc spring other than the plate spring.

The module package 2 and the holder 3 are connected to each other with a structure in which the elastic body 53 and the viscoelastic body 54 are connected in series. However, in this embodiment, the elastic body 53 is formed of the disc spring. The disc spring is so configured as to cut off an upper portion of a hollow circular cone, and generate a restoring force by collapsing the disc spring from above. Also, the viscoelastic body 54 is made of a gel material that mainly includes silicone. The gel material 54 is of a doughnut cylindrical configuration in order to prevent an interference with the cable 4*b* and the connectors 41*b*, 42*b*. The fixation of the package 2 to the disc spring 53 and the gel material 54 is conducted by using the connectors 41*b* and 42*b*. The gel material 54 is fixed to a holder cap part 3*c*. As the fixing method, an adhesive is used in this example. Also, the connection of the gel material 54 and the disc spring 53 is conducted by fixing the gel material 54 and the disc spring 53 to the front and rear surfaces of the holder cap part 3*d* with adhesives, respectively. Further, the adhesive is used to fix the holder cap 3*b* to the disc spring. The holder 3*a* and the holder cap 3*b* are fixed to each other by screwing, and the holder cap part 3*c* and the package are fixed to each other by the connectors 41*b*/42*b*. In this way, the holder 3*a* and the package 2 are connected to each other with the series connection of the disc spring 53 and the gel material 54.

The disc spring 53 can be of another configuration such as the coil spring or the plate spring. Also, the gel material can mainly contain, for example, urethane resin or vinyl resin other than silicone. Further, the viscoelastic body 54 can be of a sponge configuration or a honeycomb hollow structure. With the application of the above structures, the radiation property can be ensured in addition to the above features. As a result, the confinement of heat on the head by wearing the holder 3 can be suppressed.

The structure according to this embodiment exhibits a variation in the pressure with time as shown in FIG. 4.

That is, the pressure becomes relatively high immediately after the holder has been worn on the head, which surely brings the leading end of the light guide 21 which is disposed in the contactor 23 of each of the modules in close contact with the scalp. Thereafter, the pressure is gradually attenuated to reduce a load on the person to be examined. Further, the pressure is then held to a given pressure value, thereby firmly wearing the holder on the head. Accordingly, the light irradiation module and the light detection module can be excellently brought in close contact with the scalp without applying an excessive force to the head of the person to be examined. As a result, the measurement precision of the optical measurement is improved. Also, the uncomfortable feeling of the person to be examined is remarkably reduced, and it is possible to wear the holder in an everyday life state, and conduct the measurement on an infant, a young child, or an older person as the person to be examined. As a result, the measurable range of optical measurement that can be done on a living body is remarkably enlarged.

Seventh Embodiment

Figure 12:
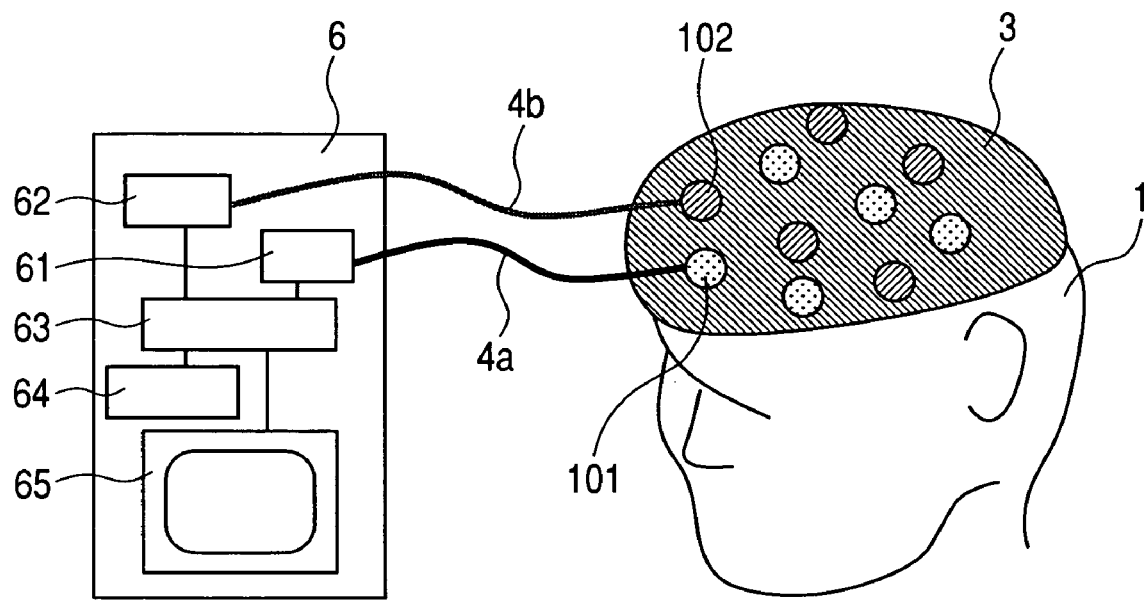
FIG. 12 is a diagram showing an entire living body optical measuring device.

Finally, a description will be given of a sixth embodiment according to the present invention with reference to FIG. 12. FIG. 12 shows the entire living body optical measuring device according to the present invention.

The person to be examined wears the holder 3, and measures a blood flow state of the brains. The holder 3 is equipped with plural light irradiation modules 101 and light detection modules 102. The leading ends of those modules 101 and 102 come in contact with the scalp 1 of the person to be examined. The light irradiation modules and the light detection modules are attached to the holder in at least any configuration of the above first to seventh embodiments. The light irradiation modules and the light detection modules are connected to a measuring device 6 through wirings. The measuring device 6 has a transmitter 61, a receiver 62, an arithmetic device 63, a storage device 64, and a display device 65. The transmitter 61 transmits an electric signal that has been modulated at a specific frequency or an optical signal that has been converted into a wavelength of a near-infrared area to each of the light irradiation modules 101. A light that has been input to the scalp 1 from the light irradiation module 101 is scattered on the surface of a cerebral cortex. However, the scattered light varies according to a change in the volume of blood in the cerebral cortex as well as the concentration of oxygenation and reduced hemoglobin in the blood. The scattered light is detected by the light detection module 102. The detected optical signal or the electric signal that has been converted in the light detection module 102 is input to the receiver 62. The receiver 62 conducts information processing between the arithmetic device 63 and the storage device 64, and calculates the amount of hemoglobin within the brains according to the signal. The calculated results are displayed on the display device 65. In this way, a change in the volume of blood on the cerebrum surface in a two-dimensional space.

With the use of the holder 3 according to the present invention, an unnecessary pressure that is applied to the person to be examined is reduced, and the module leading end is firmly brought in contact with the scalp of the person to be examined. This enables the precise measurement to be realized while reducing a load on the person to be examined.

The present invention is applied to an optical measuring device for measuring the characteristics of a living body using light, wherein the measurement probe can be brought in close contact with the person to be examined without applying excessive pressure to the person to be examined, the uncomfortable feeling of the person to be examined is reduced, and measurement precision can be improved.

What is claimed is:

1. A head-coupled holder for living body optical measurement which is worn on a head of a person to be examined, comprising:
    a light irradiation module for irradiating the head of the person to be examined with a light; and
    a light detection module adapted to detect the light which has been irradiated from the light irradiation module and propagated through the head of the person to be examined, wherein each of the light irradiation module and the light detection module includes a contactor having a contact portion that comes in contact with a scalp of the person to be examined at a leading end thereof, and exposes a leading end of a light guide to the contact portion to form the light guide, and a package having a lower portion to which the contactor is attached, wherein the holder has an insertion hole having a lower portion opened into which the package is inserted, and wherein the package is fixed to the inner upper wall of the insertion hole with a series structure of an elastic body and a viscoelastic body; and wherein the contactor is fixed to the lower portion of the package through another elastic body.

2. The head-coupled holder according to claim 1, wherein the viscoelastic body is made of a gel material.

3. The head-coupled holder according to claim 1, wherein the viscoelastic body is of a hollow structure.

4. The head-coupled holder according to claim 1, wherein the elastic body is a spring.

5. A head-coupled holder for living body optical measurement which is worn on a head of a person to be examined, comprising:

a light irradiation module for irradiating the head of the person to be examined with a light; and a light detection module adapted to detect the light which has been irradiated from the light irradiation module and propagated through the head of the person to be examined, wherein each of the light irradiation module and the light detection module includes a contactor having a contact portion that comes in contact with a scalp of the person to be examined at a leading end thereof, and exposes a leading end of a light guide to the contact portion to form the light guide; and a package having a lower portion to which the contactor is attached, wherein the holder has an insertion hole having a lower portion opened into which the package is inserted, and wherein the package is fixed to an inner upper wall of the insertion hole through a series of elastic bodies, and the contactor is fixed to the lower portion of the package through another elastic body.

6. The head-coupled holder according to claim 5, wherein the elastic body is a spring.

7. The head-coupled holder according to claim 5, wherein the viscoelastic body is made of a gel material.

8. The head-coupled holder according to claim 5, wherein the viscoelastic body is of a hollow structure.

* * * * *